US012201845B2

(12) United States Patent
Fischer et al.

(10) Patent No.: US 12,201,845 B2
(45) Date of Patent: Jan. 21, 2025

(54) ANCHOR SYSTEM FOR RETAINING A DEVICE IN TISSUE

(71) Applicant: INCUBE LABS, LLC, San Jose, CA (US)

(72) Inventors: Elmar Fischer, Boerne, TX (US); Robert Gaffney, San Jose, CA (US); Varghese K. George, San Jose, CA (US); Kyle Horlen, Shavano Park, TX (US); Mir A. Imran, Los Altos Hills, CA (US); Charles Gregory Nelson, New Braunfels, TX (US); Paul Spehr, San Antonio, TX (US)

(73) Assignee: InCube Labs, LLC, San Jose, CA (US)

( * ) Notice: Subject to any disclaimer, the term of this patent is extended or adjusted under 35 U.S.C. 154(b) by 454 days.

(21) Appl. No.: 17/610,095

(22) PCT Filed: May 7, 2020

(86) PCT No.: PCT/US2020/031922
§ 371 (c)(1),
(2) Date: Nov. 9, 2021

(87) PCT Pub. No.: WO2020/227560
PCT Pub. Date: Nov. 12, 2020

(65) Prior Publication Data
US 2022/0241599 A1 Aug. 4, 2022

Related U.S. Application Data

(60) Provisional application No. 62/944,315, filed on Dec. 5, 2019, provisional application No. 62/942,006, filed on Nov. 29, 2019, provisional application No. 62/845,814, filed on May 9, 2019, provisional application No. 62/845,811, filed on May 9, 2019, (Continued)

(51) Int. Cl.
*A61N 1/375* (2006.01)
*A61N 1/05* (2006.01)

(52) U.S. Cl.
CPC ....... *A61N 1/37518* (2017.08); *A61N 1/0558* (2013.01)

(58) Field of Classification Search
CPC .............. A61N 1/37518; A61N 1/0558; A61N 1/0539; A61N 1/057; A61N 1/059
See application file for complete search history.

(56) References Cited

U.S. PATENT DOCUMENTS 4,848,352 A 7/1989 Pohndorf et al.
5,954,761 A 9/1999 Machek et al.
(Continued)

OTHER PUBLICATIONS

International Search Report and Written Opinion for Application No. PCT/US2020/031922, dated Aug. 4, 2020, 10 pages.

*Primary Examiner* — Eugene T Wu
(74) *Attorney, Agent, or Firm* — Brooks Kushman P.C.

(57) ABSTRACT

A lead device is provided for a medical treatment apparatus, where the lead device includes protruding anchoring mechanisms for anchoring the lead device in tissue. The anchoring mechanism include permanent anchoring mechanisms, or a combination of permanent and dissolvable anchoring mechanisms, to anchor the device in tissue. The anchoring mechanism resists migration of the lead device in at least one or both axial directions.

20 Claims, 9 Drawing Sheets

Related U.S. Application Data provisional application No. 62/845,823, filed on May 9, 2019.

(56) References Cited

U.S. PATENT DOCUMENTS

| | | | |
|---|---|---|---|
| 2004/0215306 A1 | 10/2004 | Heil, Jr. et al. | |
| 2005/0096718 A1* | 5/2005 | Gerber | A61N 1/0558 607/117 |
| 2005/0182472 A1 | 8/2005 | Wahlstrom et al. | |
| 2006/0020317 A1* | 1/2006 | Flach | A61N 1/0573 607/130 |
| 2007/0270928 A1* | 11/2007 | Erlebacher | A61N 1/057 607/126 |
| 2008/0183257 A1* | 7/2008 | Imran | A61N 1/0558 607/117 |
| 2008/0183267 A1* | 7/2008 | D'Aquanni | A61N 1/057 607/127 |
| 2010/0010550 A1* | 1/2010 | Ponomarev | A61N 1/0529 607/2 |
| 2013/0231727 A1* | 9/2013 | Carlson | A61L 31/022 607/126 |

\* cited by examiner

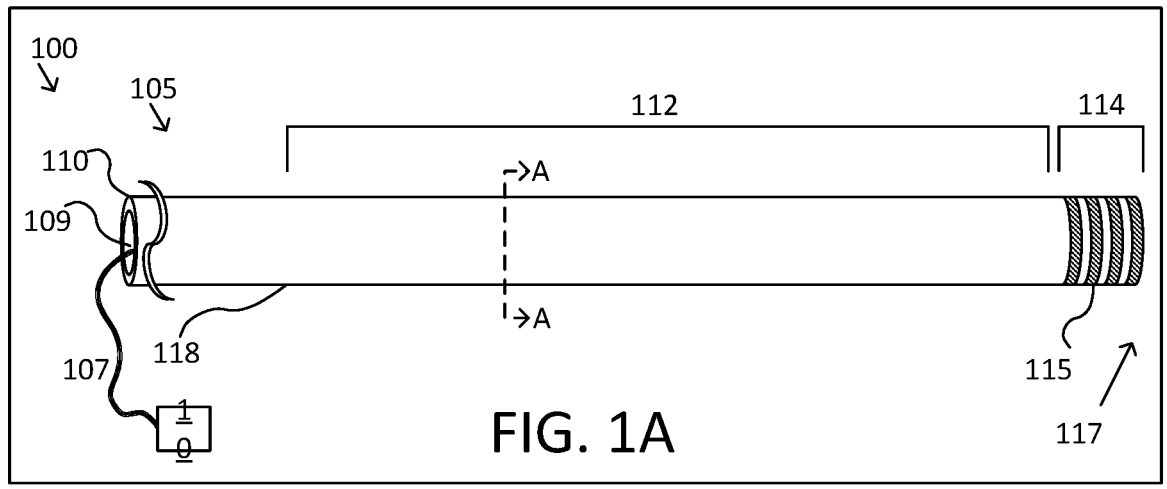
FIG. 1A
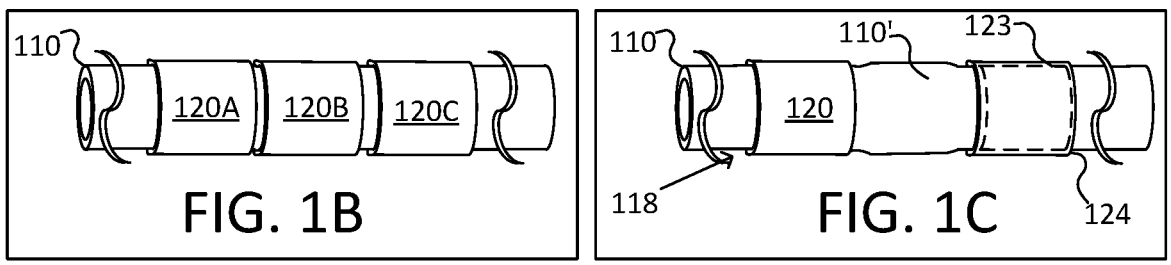
FIG. 1B
FIG. 1C
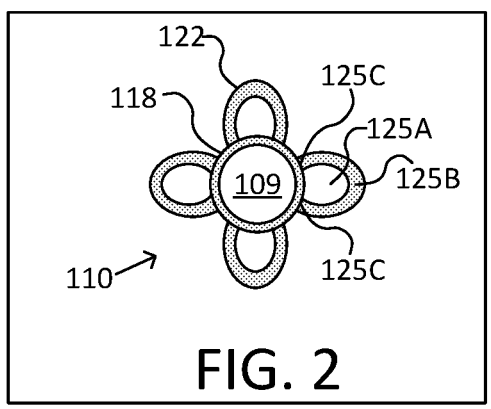
FIG. 2
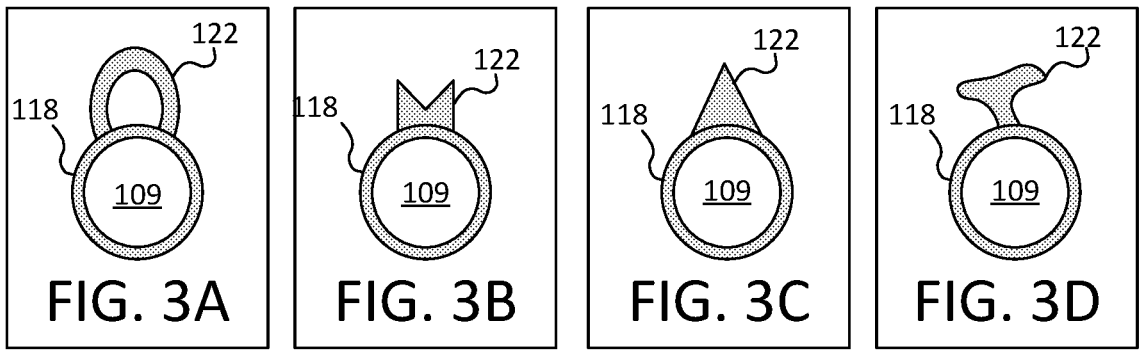
FIG. 3A  FIG. 3B  FIG. 3C  FIG. 3D

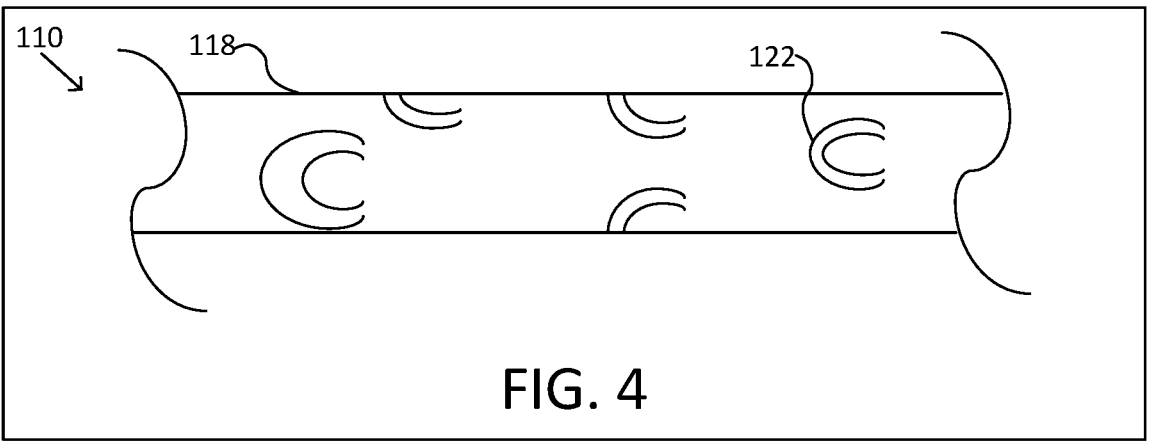
FIG. 4
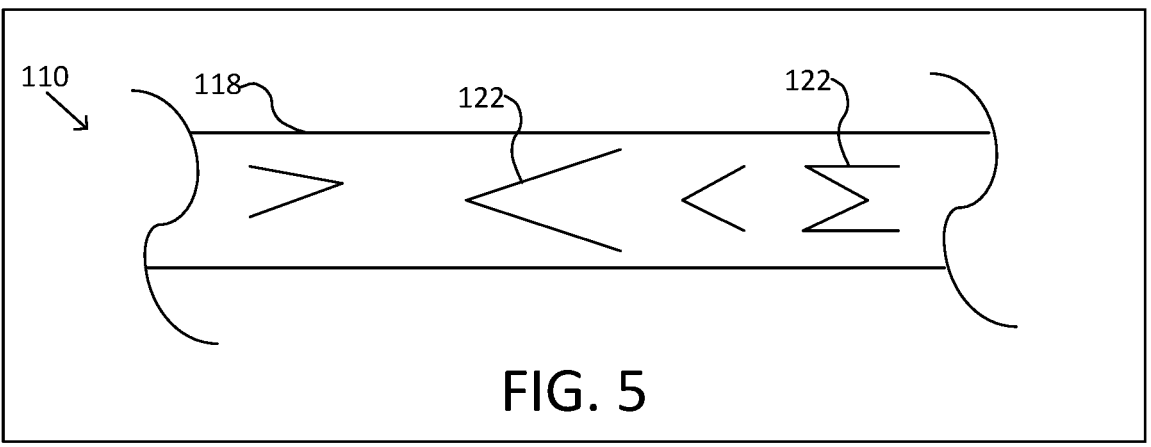
FIG. 5
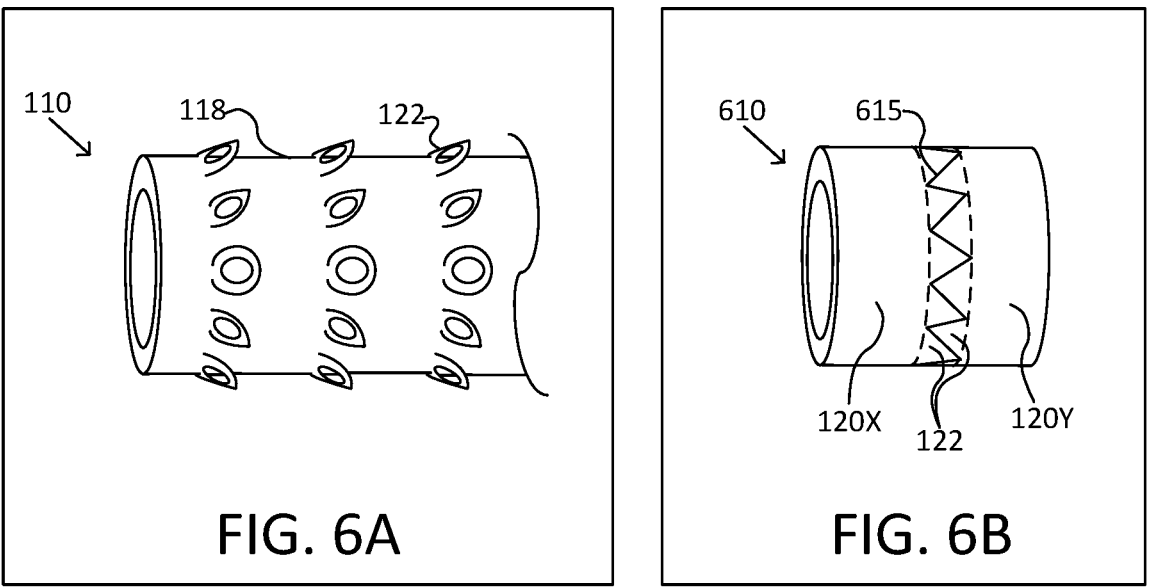
FIG. 6A
FIG. 6B

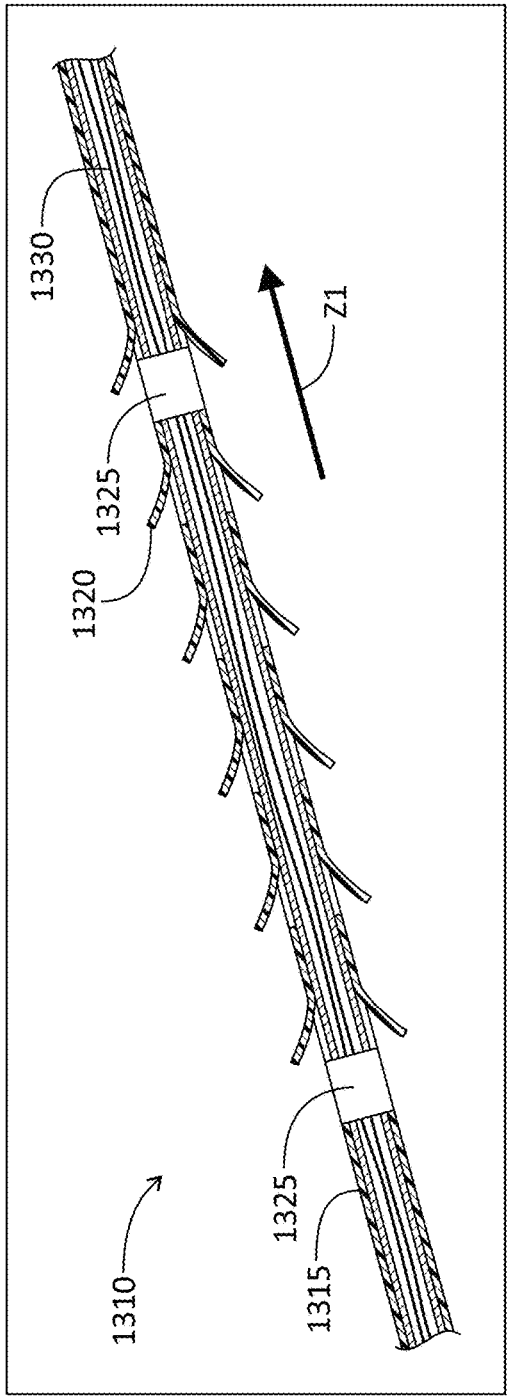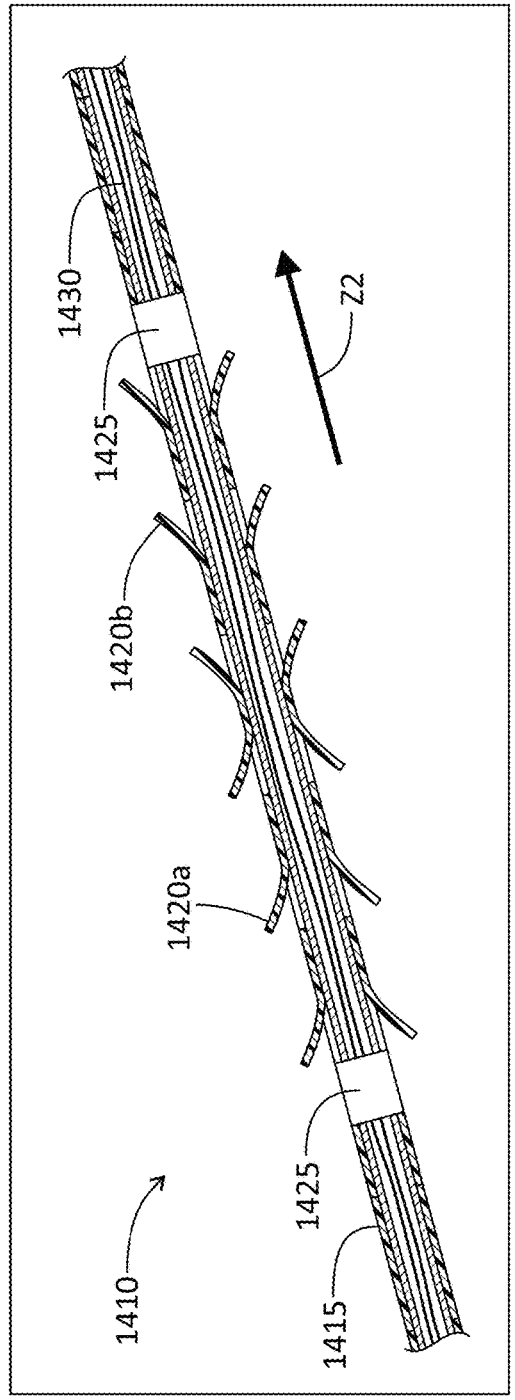
FIG. 13
FIG. 14

ANCHOR SYSTEM FOR RETAINING A DEVICE IN TISSUE

CROSS-REFERENCE TO RELATED APPLICATIONS

This application is the U.S. National Phase of PCT Application Ser. No. PCT/US2020/031922filed on May 7, 2020, which is the U.S. National Phase of PCT Application No. PCT/US2020/031922 filed on May 7, 2020, which claims the benefit of U.S. Provisional Application No. 62/845,811, filed on May 9, 2019, U.S. Provisional Application No. 62/845,814, filed on May 9, 2019, U.S. Provisional Application No. 62/845,823, filed on May 9, 2019, U.S. Provisional Application No. 62/942,006, filed on Nov. 29, 2019, and U.S. Provisional Application No. 62/944,315, filed on Dec. 5, 2019, the disclosures of which are hereby incorporated in their entirety by reference herein.

FIELD

Embodiments relate to an anchoring structure for an implanted medical device. Embodiments include permanent anchoring mechanisms, or a combination of permanent and dissolvable anchoring mechanisms, to anchor the device in tissue.

BACKGROUND

With advances in medical technology there has been an increasing use of various implantable biomedical devices, such as, for example, for delivering stimulatory and other electrical signals to tissue for the treatment of various medical conditions. Many of these devices employ a cord, catheter, lead or other device extended into tissue within an animalia body, for purposes of applying medical treatment through a treatment region of the device. For example, in some medical applications, an electrode is provided at the distal end of a device, and the device is introduced into the body with the distal end being advanced to reach a target region. In such applications, the target region may be adjacent to a nerve for electrical stimulation to the nerve, and relatively precise positioning of the electrode near the nerve may be important for the treatment to be effective.

Additionally, in many medical applications, a device for such medical applications may be maintained in the body for an extended period of time. For example, a device for providing stimulation for a medical treatment can be maintained in the body for days, weeks or even indefinitely, depending on the treatment provided. In such applications, the length of time that the device remains in place to stimulate the target region can extend past a period after which the body begins to react to the introduction and continued presence of the device. The physiological reactions can include, for example, movement or settlement of tissue surrounding the device, as well as fluid build-up and/or formation of scar tissue in an area around the device. Such physiological reactions can cause movement (e.g., migration) of the device, which can result in an effectiveness of the medical treatment being reduced, delivery of stimulation to the wrong tissue, an allergic reaction, or other unwanted immune response and/or infection of the implantation site. Further, body movement can also result in movement of the device. Thus, there is a need for anchoring of implanted devices within the body at the target region to resist movement of the implanted devices.

SUMMARY

In an aspect, a lead device of a medical device includes a first set of surface elements and a second set of surface elements. The first set includes one or more biodegradable surface elements configured to protrude from the lead device upon deployment; and the first set is designed to resist movement of the lead device upon deployment and for a designed time thereafter until the first set biodegrades in vivo. The second set includes one or more non-biodegradable surface elements configured to protrude from the lead device upon deployment; and the second set is designed to promote tissue growth around the surface elements within the designed time for the first set to biodegrade in vivo.

The surface elements of the second set may each include a strip of material attached at both ends of the strip to the lead device, thereby forming a void between the strip and the lead device; the strip of material and the void designed to promote tissue growth around the surface element, including within the void. The lead device may include two joints for each surface element of the second set, one joint at each end of the strip where the strip is attached to the lead device, wherein at least one of the two joints associated with each surface element of the second set are designed to break, after tissue growth has occurred around the surface element, and upon exertion of a pulling force axially along the lead device. One or more of the surface elements of the first set include a metal; the metal may be magnesium. One or more of the surface elements of the first set include a polymer. The polymer may include one or both of poly(lactic acid) (PLA) or polycaprolactone (PCL).

In an aspect, a lead device of a medical device includes a lead shaft with a perimeter shell having a fixation region and a treatment region, the lead shaft defining a channel configured to accept at least one electrical conductor, and an electrode in the treatment region, the electrode configured to be electrically connected to the conductor. The lead device may include a patterned sleeve forming a portion of the fixation region of the perimeter shell; and multiple biodegradable surface elements on the patterned sleeve, each biodegradable surface element designed to resist movement of the lead device upon deployment and for a designed time thereafter until biodegradation of the biodegradable surface element The perimeter shell may include multiple non-biodegradable surface elements, each non-biodegradable surface element shaped to promote tissue growth around and through the non-biodegradable surface element. At least one of the non-biodegradable surface elements may include a strip of non-biodegradable material, each end of the strip may be attached to the perimeter shell at a respective joint, and at least one joint may be configured to break when the lead device is subjected to a pulling force after tissue growth has occurred around and through the non-biodegradable surface element. The lead device may include multiple treatment regions of the perimeter shell, where the treatment region is a first treatment region of the multiple treatment regions. The lead device may include multiple fixation regions of the perimeter shell, wherein the fixation region is a first fixation region of the multiple fixation regions. The lead device may include a second fixation region of the multiple fixation regions, where the second fixation region includes multiple non-biodegradable surface elements. The lead device may include multiple non-biodegradable surface elements disposed in the first fixation region. The lead device may include multiple treatment regions of the perimeter shell and multiple fixation regions of the perimeter shell, where the treatment region is a first treatment region of the multiple treatment regions and wherein the fixation region is a first fixation region of the multiple fixation regions. The multiple treatment regions may be interspersed between ones of the multiple fixation regions.

In an aspect, a lead device of a medical device includes a lead shaft including a perimeter shell having a fixation region and a treatment region; an electrode in the treatment region; multiple non-biodegradable surface elements disposed in the fixation region; and a biodegradable sleeve covering the non-biodegradable surface elements.

The biodegradable sleeve may be configured to biodegrade over a predefined time period such that at the end of the time period the biodegradation has progressed sufficiently to allow the non-biodegradable surface elements to be released from a biased state. The non-biodegradable surface elements may be held in the biased state by the presence of the biodegradable sleeve, and after being released from the biased state protrude from the perimeter shell. The lead device may include biodegradable surface elements disposed on the biodegradable sleeve, the biodegradable surface elements configured to engage tissue at a target site when deployed such that the lead device resists movement.

Embodiments include a lead device for use with a medical device. The lead device includes a lead shaft and an electrode. The lead shaft includes a perimeter shell having a fixation region and a treatment region, with the electrode disposed in the treatment region. The perimeter shell includes a plurality of surface elements disposed in the fixation region, with at least a portion of the perimeter shell being biodegradable.

BRIEF DESCRIPTION OF THE DRAWINGS

FIG. 1A illustrates an example of an embodiment of a medical apparatus including a lead device.

FIG. 1B illustrates an example of an embodiment of a lead device including multiple patterned sleeves.

FIG. 1C illustrates an example of an embodiment of a lead device including a biodegradable sleeve over a patterned portion of the lead device.

FIG. 2 illustrates an example of an embodiment of a surface element pattern on a lead device.

FIG. 3A illustrates an example of an embodiment of a surface element on a lead device.

FIG. 3B illustrates an example of another embodiment of a surface element on a lead device.

FIG. 3C illustrates an example of another embodiment of a surface element on a lead device.

FIG. 3D illustrates an example of another embodiment of a surface element on a lead device.

FIG. 4 illustrates an example of a pattern of surface elements, according to one or more embodiments.

FIG. 5 illustrates an example of another pattern of surface elements, according to one or more embodiments.

FIG. 6A illustrates an example of a repeating pattern of surface elements, according to one or more embodiments.

FIG. 6B illustrates an example of a pattern on a sleeve for a lead device, according to one or more embodiments.

FIG. 13 illustrates an example of a lead device with multiple surface elements arranged unidirectionally.

FIG. 14 illustrates an example of a lead device with multiple surface elements arranged bidirectionally.

FIG. 1B illustrates an example of a lead device.

DETAILED DESCRIPTION

Figure 7A:
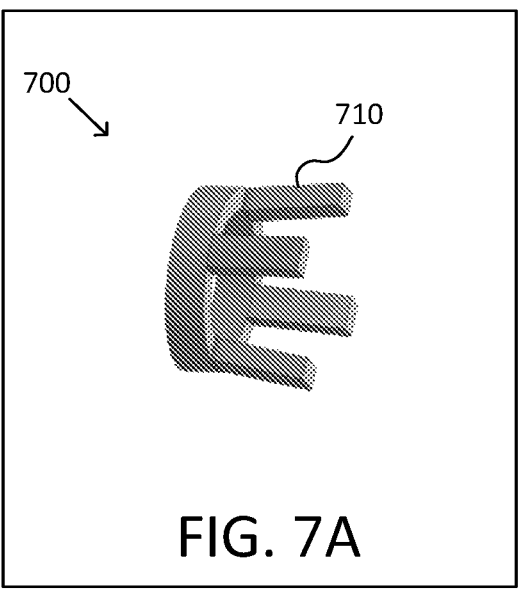
FIG. 7A illustrates an example of a sleeve for a lead device, according to one or more embodiments.

Various embodiments include a medical treatment apparatus including protruding surface elements to anchor a portion of the apparatus in tissue.

In one or more embodiments of a medical treatment application or process, a medical treatment apparatus can include, for example, a cord, catheter, lead or other device (for convenience hereinafter, referred to as a lead device) which can be introduced into an animalia body, such that a treatment portion of the lead device is positioned at a target location within the body. A few examples of target locations are proximate the spinal cord, heart, stomach, or bladder, or proximate a nerve or muscle. The introduction of the lead device can be performed by a doctor or medical professional, often through the use of an imaging modality (e.g., fluoroscopy, ultrasound, endoscopic image capture, or other imaging technique) or sensing devices that allow attending personnel to position the treatment section of the lead device relatively precisely at the target location. In one or more embodiments, the implantation process may involve use of a separate implantation device (e.g., an introducer) which can provide a conduit or path for the lead device as it is introduced. Once the lead device is positioned at the target location, the implantation device can be removed. It may then be desirable for the lead device to retain its position for days, weeks, months or years with little movement, to improve eventual success of the treatment being applied.

As an example of an embodiment of a medical treatment application or process, a lead device may be implanted alongside a nerve to provide electrical stimulation to the nerve, (e.g., for pain management, for blocking of signal conduction along the nerve to avoid a responsive action by the body, or to activate signal conduction in the nerve), or alongside a muscle (e.g., to allow or to inhibit muscle contraction), or at other sites. Implantation may be performed, for example, by using an introducer to deliver the lead device, and removing the introducer once the lead device is positioned, thereby allowing anchoring mechanisms of the lead device to deploy. In one or more embodiments, a stimulation controller in electrical communication with the lead device may provide energy for, and control, electrical stimulation provided by the lead device.

While the static positioning of lead devices in tissue can be important for the effectiveness of the respective treatment, the dynamic nature of a living body can make effective anchoring of such lead devices challenging. A common challenge with implanted lead devices is movement, where the lead device is moved after being positioned at the target location by body movement, by external forces being applied to the body, or by external forces being applied to a controller connected to the lead device which forces propagate to the lead device. An anchoring mechanism can be desirable to resist such movement of the lead device.

Discussed below are embodiments of anchoring mechanisms that resist movement, such as resisting movement of a lead device or another apparatus on which the anchoring mechanism is attached, disposed, affixed, connected, formed, or otherwise incorporated (any such relationship hereinafter referred to for convenience as incorporated). For convenience, resistance to movement is discussed hereafter in terms of resistance to axial movement or migration of a lead device. It is to be understood, however, that the anchoring mechanisms contemplated by this disclosure resist other forms of movement as well, and are applicable to apparatuses other than lead devices.

Axial migration may be retrograde or antegrade. Retrograde migration refers to axial movement of a lead device away from a target treatment location, while antegrade migration refers to axial movement towards the target location. Either type of migration can reduce effectiveness of the medical treatment being provided. Various factors can contribute to forces that cause such migration. These include, for example, the reaction of tissue in the body (e.g., settlement of tissue, formation of scar tissue) to the presence or movement of the lead device, as well as body movement and typical dynamic fluctuations within a body.

To minimize lead device migration, one or more anchors may be incorporated with or on the lead device to anchor the lead device within body tissue. When implanted, the anchoring mechanism resists migration of the lead device in at least one or both axial directions.

In various embodiments, the lead device may include an arrangement of anchoring mechanisms, such as surface elements, where the arrangement includes a first set of surface elements having a first axial orientation, and a second set of surface elements having a second axial orientation.

In one or more embodiments, a medical treatment apparatus is operated by advancing an introducer into a body, where the introducer includes a lumen that retains a lead device, and the lead device includes a shaft with protruding surface elements. When retained by the lumen, the individual surface elements are forced inwards, so as to be under bias. Using the introducer, the lead device is advanced until the lead device reaches a target region within the body. When the lead device reaches the target region, the introducer may be removed to allow the surface elements to release outward into an unbiased state.

FIG. 1A illustrates a medical apparatus 100 including an optional controller 10 and a lead device 105 including a lead shaft 110 having a channel 109 (lumen) extending therethrough. The lead device 105 in the embodiment of FIG. 1A includes a fixation region 112 and a treatment region 114 which incorporates one or more electrodes 115 (four are shown) at a distal end 117 of the lead shaft 110. In other embodiments, the fixation region 112 and/or the treatment region 114 may be at different locations along the lead shaft 110, and/or there may be multiple instances of the fixation region 112 for fixation at different locations along the lead shaft 110, and/or there may be multiple instances of the treatment region 114 for applying treatment from different locations along the lead shaft 110. For example, multiple electrodes 115 may be positioned along the lead shaft 110, with one or more treatment regions 114 interspersed between the electrodes 115 or between sets of the electrodes 115, where a number of electrodes in a set may be equal or different than a number of electrodes in another set.

In an embodiment, the lead shaft 110 has a diameter in a range of about 0.03 inches to about 0.04 inches (e.g., equal to or less than 1 millimeter (mm)).

Controller 10 may be in electrical communication with the electrode(s) 115 to provide energy to the electrode(s) 115 in a controlled fashion. For example, the controller 10 may be used to provide and control energy for electrical stimulation treatment, such as to nerve endings, muscles, or organs. In embodiments including the optional controller 10, a conductor 107 (e.g., a wire or multiple wires, or a printed pattern, or other electrical/signal connection) may extend from the controller 10 through channel 109 of the lead shaft 110 to the electrode(s) 115, to activate the electrode(s) 115 in accordance with a treatment plan.

The lead shaft 110 can be introduced at a position and to a depth where the electrode(s) 115 are sufficiently proximate to a target region where stimulation is to be provided as treatment. For at least some treatments (e.g., treatments that include stimulation of nerves), precision placement of the electrode can be important for the treatment to be effective, and migration of the lead shaft 110 can result in reduced effectiveness of the treatment, or inadvertent effects.

The lead shaft 110 includes a perimeter shell 118. In one or more embodiments, a portion of the perimeter shell 118 may be formed separately from a remainder of the lead shaft 110 of the lead device 105. In one or more embodiments, a portion of the perimeter shell 118 can correspond to a thickness that is unitarily formed or otherwise integrated with the lead shaft 110. For example, portions of the perimeter shell 118 can be provided using a sleeve, where the sleeve is wrapped, fitted or otherwise formed over the lead shaft 110; and/or portions of the perimeter shell 118 can be formed as part of unibody lumen structure of the lead shaft 110. The fixation region(s) 112 are incorporated into the perimeter shell 118.

FIG. 1B illustrates an example of an embodiment in which one or more patterned sleeves 120 (specifically in this example patterned sleeves 120A, 120B, 120C) are positioned on the lead shaft 110. The patterned sleeves 120 may have similar patterns or different patterns with respect to each other, and may be formed of similar materials or different materials with respect to each other and with respect to the lead shaft 110. For example, the patterned sleeves 120A and 120C may be similar to each other in material and pattern, whereas the patterned sleeve 120B is different from the patterned sleeves 120A and 120C in one or both of material and pattern. For another example, each of the patterned sleeves 120A, 120B, and 120C may be different from each other in material and/or pattern.

In one or more embodiments, one or more patterned sleeves 120 are made from a biodegradable material (e.g., breaks down or dissolves in vivo) and one or more patterned sleeves 120 are made from a material that is not biodegradable. The patterned sleeves 120 which are biodegradable include biodegradable protrusions shaped to engage with tissue at a target site to provide for an immediate anchoring of the lead shaft 110 in the tissue, which serves to hold the lead shaft 110 in a desired position until the protrusions biodegrade. The patterned sleeves 120 which are not biodegradable include non-biodegradable protrusions shaped to promote tissue growth around the protrusions over a period of time; the same protrusions may additionally assist in immediate anchoring of the lead shaft 110 at the desired position.

Biodegradable protrusions are designed to biodegrade over a time sufficient to allow tissue growth to occur around the non-biodegradable protrusions, such that the lead shaft 110 is held in the desired position by the tissue growth around the non-biodegradable protrusions before the biodegradable protrusions have completed their biodegradation.

In one or more embodiments, a biodegradable sleeve may include non-biodegradable protrusions, and a non-biodegradable sleeve may include biodegradable protrusions. For example, a patterned sleeve 120 may be non-biodegradable, with biodegradable protrusions affixed. For another example, a patterned sleeve 120 may be non-biodegradable, with both biodegradable protrusions affixed and non-biodegradable protrusions affixed or otherwise incorporated; in such an embodiment, the biodegradable and non-biodegradable protrusions may be separate from each other, or interspersed with each other.

FIG. 1C illustrates an example of an embodiment in which non-biodegradable protrusions are formed into the lead shaft 110, such as along a portion 110', and biodegradable protrusions are provided on one or more patterned sleeves 120 positioned over the lead shaft 110.

FIG. 1C further illustrates an example of an embodiment in which the perimeter shell 118 includes a portion 123 (either incorporated with the lead shaft 110 or as a sleeve over the lead shaft 110) with non-biodegradable protrusions, and a biodegradable sleeve 124 (with or without protrusions), where the sleeve 124 is positioned over the non-biodegradable protrusions of the portion 123, and the non-biodegradable protrusions of the portion 123 are retained under bias (in a non-protruded state) by the sleeve 124. In such an embodiment, the sleeve 124 biodegrades over time until the non-biodegradable protrusions of the portion 123 are able to deploy outward from the lead device into a relaxed state. The biodegradable sleeve 124 may be used, for example, over a patterned area of the perimeter shell 118 in FIG. 1A, or over a patterned sleeve 120 in FIG. 1B. In one or more embodiments, the sleeve 124 may be used to reduce long-term anchoring via tissue growth around a portion of the non-biodegradable protrusions of the portion 123 of the lead shaft 110 until after a trial period of implantation of the lead device 105.

In one or more embodiments, the lead shaft 110 is formed to have a material thickness of the lead shaft 110 under a patterned sleeve 120 that is less than a material thickness of other portions of the lead shaft 110 (such as is illustrated in FIG. 1C, where a material thicknesses of the lead shaft 110 under the sleeves 120 and 124 are less than a material thickness of the lead shaft 110 along the portion 110'). In this manner, an outer diameter of the perimeter shell 118 may be approximately consistent, or may be substantially similar, along a segment of the lead shaft 110.

For convenience, protrusions, whether biodegradable or non-biodegradable, are referred to with respect to FIGS. 2, 3A-3D, and 4-7 as surface elements 122.

FIG. 2 illustrates an example of a pattern of deployed surface elements 122 as viewed down a long axis of the lead shaft 110 at a cross-section of the lead shaft 110 in one or more embodiments, such as at a cross-section along line A-A in FIG. 1A in one or more embodiments. In this example, multiple (here, four) hollow petal-shaped surface elements 122 extend from the perimeter shell 118. Each petal-shaped surface element 122 includes a void 125A surrounded by an arc 125B (e.g., an arcuately shaped strip of material) joining the remainder of the perimeter shell 118 at joints 125C. The arcuate shape of the arc 125B is provided by way of example, and other shapes besides an arcuate shape are also encompassed by the present disclosure. In an embodiment in which the surface elements 122 are cut into the perimeter shell 118 (which includes cutting the surface elements 122 into a sleeve of the perimeter shell 118), joints 125C may be formed at the junction between the cutout portion and the remainder of the perimeter shell 118. In an embodiment in which the surface elements 122 are affixed to the perimeter shell 118 (including onto a sleeve of the perimeter shell 118), the joints 125C are at a junction where the surface elements 122 are affixed to the perimeter shell 118.

In one or more embodiments, a petal-shaped surface element 122 (e.g., as illustrated in FIG. 2) is non-biodegradable, and the strip of material forming the arc 125B around the void 125A is designed to promote tissue growth around the surface element 122, including within the void 125A. When deployed at a target site, the surface element 122 provides deterrence against movement axially, and as tissue grows into and around the void 125A, the surface element 122 further provides deterrence against movement in all directions. If the lead shaft 110 is later to be explanted (removed), the lead shaft 110 may be pulled, and the surface element 125 and the tissue growth around it may resist against the pulling. In an embodiment, the arc 125B of the surface element 122 is designed to separate from the remainder of the perimeter shell 118 at one or both of the joints 125C due to a designed thinness of the material at the joint(s)125C; the thinness of the material is designed to allow a break of the joint(s) 125C at a predefined pull force threshold. In this manner, the surface element 122 can provide for anchoring of the lead shaft 110 during normal motion of a subject in which the lead shaft 110 is implanted, and can further provide for explanting of the lead shaft 110 if desired. In one or more embodiments, the strip of material forming the arc 125B around the void 125A is not continuous and rather is formed in two lengths; the two lengths may meet at respective ends of the two lengths, or the two lengths may overlap each other. In one or more embodiments, the strip of material forming the arc 125B is connected at a single joint 125C rather than at two joints 125C.

FIGS. 3A-3D illustrate embodiments of a single surface element 122 on a cross-sectional slice of the lead shaft 110 as viewed down the long axis of the lead shaft 110. Many other designs are also within the scope of the present disclosure. In FIG. 3A, a single petal-shaped surface element 122 is shown; in FIG. 3B, a single pennant-shaped surface element 122 is shown; in FIG. 3C, a single triangle-shaped surface element 122 is shown; in FIG. 3D, a T-shaped surface element 122 is shown. In embodiments of the lead device 105, multiple surface elements 122, such as one of or a combination of the types illustrated in FIGS. 3A-3D or other designs, are incorporated into or onto the perimeter shell 118 of the lead shaft 110.

FIG. 4 illustrates an example of an embodiment of the lead shaft 110 in which the perimeter shell 118 includes a pattern of petal-shaped surface elements 122 cut or otherwise formed in, or attached to, the material of the perimeter shell 118. The surface elements 122 are shown in a biased state for convenience of discussion. In the illustration of FIG. 4, the positioning of the surface elements 122 is random, and the sizes of the surface elements 122 vary. In other embodiments, the positioning of the surface elements 122 follows a defined pattern, such as forming columns and/or rows, and/or the sizes of the surface elements 122 are similar.

FIG. 5 illustrates an example of an embodiment of the lead shaft 110 in which the perimeter shell 118 includes a pattern of triangle-shaped and pennant-shaped surface elements 122 cut or otherwise formed in, or attached to, the material of the perimeter shell 118. The surface elements 122 are shown in a biased state for convenience of discussion. In the illustration of FIG. 5, the positioning of the surface elements 122 is random, and the sizes (and shapes) of the surface elements 122 vary. In other embodiments, the positioning of the surface elements 122 follows a defined pattern, such as forming columns and/or rows, and/or the sizes and/or shapes of the surface elements 122 are similar.

FIG. 6A illustrates an example of an embodiment of the lead shaft 110 in which the perimeter shell 118 includes a pattern of petal-shaped surface elements 122 cut or otherwise formed in, or attached to, the material of the perimeter shell 118. In the illustration of FIG. 6A, positioning of the surface elements 122 follows a defined column/row structure, and sizes of the several surface elements 122 are similar. The surface elements 122 are shown in a relaxed (unbiased) state in FIG. 6A, such that the surface elements 122 protrude.

FIG. 6B illustrates an example of a tube 610 in which a pattern 615 has been cut or otherwise formed in the material of the tube 610, and extends through the tube 610 such that the tube 610 may be separated to form a patterned sleeve 120X and a patterned sleeve 120Y. After separation, the pattern 615 defines surface elements 122 on each of the patterned sleeve 120X and the patterned sleeve 120Y which, when deployed, protrude (see, for example, the patterned sleeve 810 in FIG. 8).

FIG. 7A illustrates in perspective view an embodiment of patterned sleeve 700 including surface elements 710 that are approximately rectangular in cross-section.

Figure 7B:
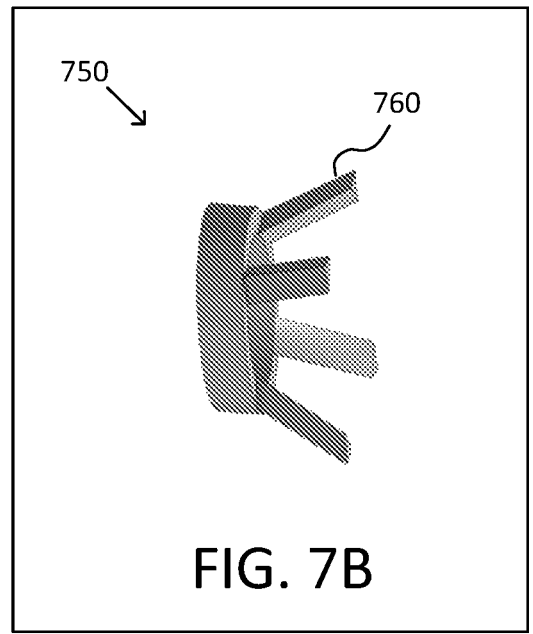
FIG. 7B illustrates an example of a sleeve for a lead device, according to one or more embodiments.

FIG. 7B illustrates in perspective view an embodiment of patterned sleeve 750 including surface elements 760 that are approximately triangular in cross-section.

Figure 8:
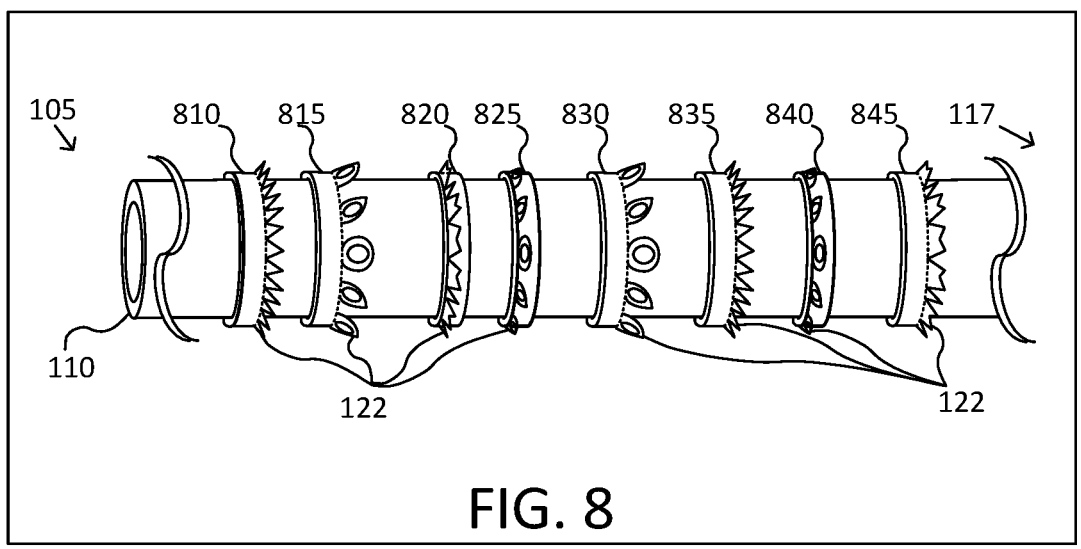
FIG. 8 illustrates an example of multiple patterned sleeves positioned along a lead device, according to one or more embodiments.

FIG. 8 illustrates an embodiment of the lead device 105 including the lead shaft 110 and multiple examples of embodiments of patterned sleeves 120, identified individually as patterned sleeves 810, 815, 820, 825, 830, 835, 840, and 845, each with deployed surface elements 122. In this embodiment of the lead device 105, some of the patterned sleeves 120 are oriented facing the distal end 117 to resist antegrade movement towards the distal end 117 (e.g., patterned sleeves 810, 815, 830, 835, and 845), while some are oriented in the opposite direction (e.g., patterned sleeves 820, 825, and 840) to resist retrograde movement away from the distal end 117. Any of the patterned sleeves 810, 815, 820, 825, 830, 835, 840, and 845 may be biodegradable, and any may be non-biodegradable. Further, any of the surface elements 122 may be biodegradable or non-biodegradable (e.g., a biodegradable surface element 122 affixed to a biodegradable or non-biodegradable sleeve 810, 815, 820, 825, 830, 835, 840, or 845, or a non-biodegradable surface element 122 affixed to a biodegradable or non-biodegradable sleeve 810, 815, 820, 825, 830, 835, 840, or 845).

In one example of the embodiment of FIG. 8, the patterned sleeves 810, 820, 835, and 845 may be biodegradable, included to provide a greater initial resistance to movement than would be provided without their inclusion. Over time, tissue growth through the voids (see, e.g., the voids 125A of FIG. 2) of the surface elements 122 on the non-biodegradable patterned sleeves 815, 825, 830, and 840 may provide increased resistance to movement than would be provided by the patterned sleeves 815, 825, 830, and 840 initially, and the patterned sleeves 810, 820, 835, and 845 may no longer be needed. Further, the petal-shaped surface elements 122 may be designed for breakage away from the lead shaft 110 when pulled at a force greater than a design threshold force (see, e.g., the illustration and description of the joints 125C in FIG. 2), to allow for explanting the lead device 105 after tissue growth has occurred.

Figure 9:
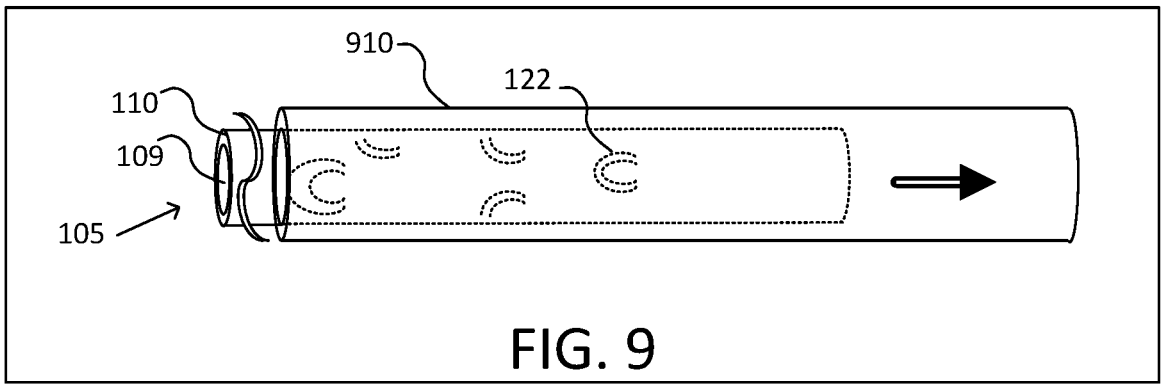
FIG. 9 illustrates an introducer for covering a lead device while the lead device is being implanted, according to one or more embodiments.

FIG. 9 illustrates an introducer 910 for covering a lead device 105 while the lead device 105 is being implanted, according to one or more embodiments. A lead device similar to the one illustrated in the embodiment of FIG. 4 is shown for the lead device 105 by way of example; the introducer 910 is applicable for other embodiments as well. The lead shaft 110 is positioned within the introducer 910 such that the surface elements 122 are biased by the introducer 910 against their natural or relaxed state of protruding radially outwards from the lead device 105.

Figure 10:
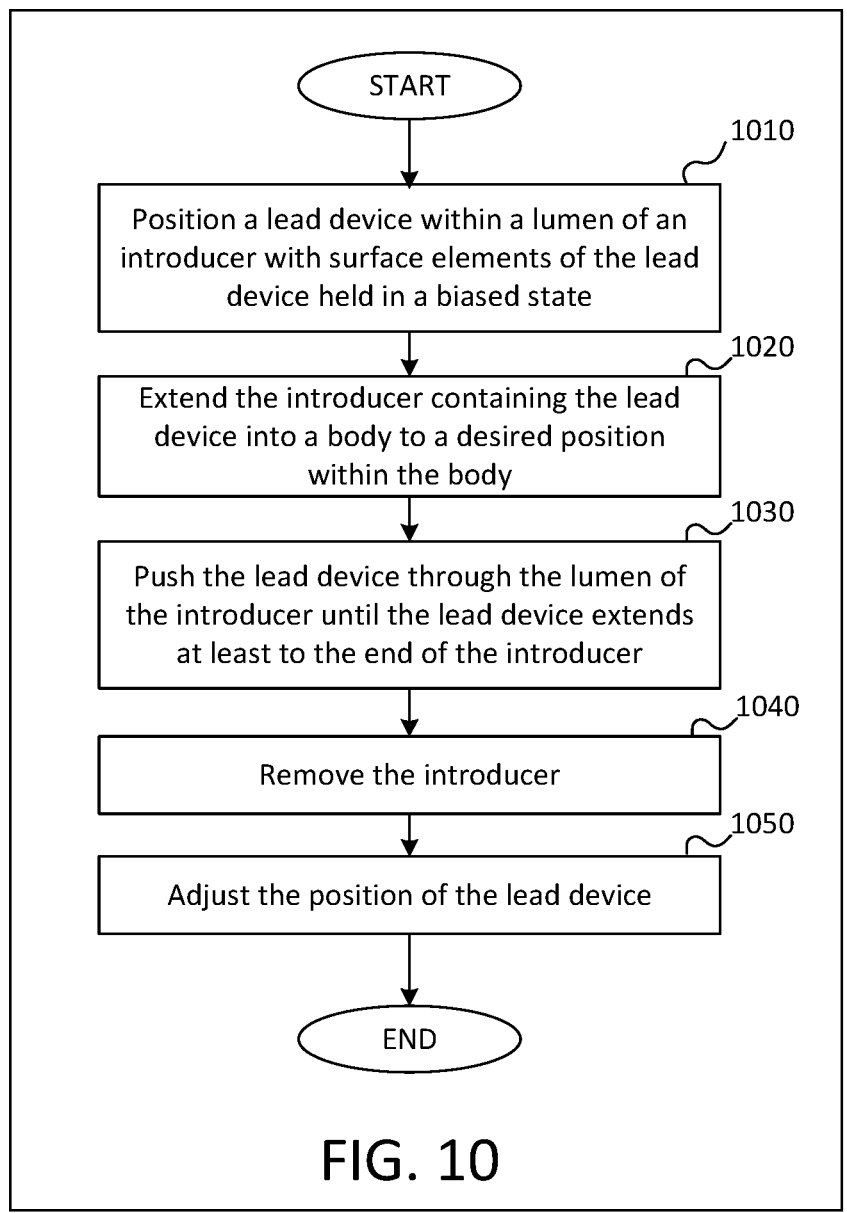
FIG. 10 illustrates a method for implanting a lead device, according to one or more embodiments.

FIG. 10 illustrates a method for implanting a lead device using an introducer such as the introducer 910, according to one or more embodiments. At 1010, a lead device (e.g., an embodiment of the lead device 105) is positioned within a lumen of an introducer (e.g., an embodiment of the introducer 910) such that the surface elements 122 are biased by the introducer against their natural or relaxed state of protruding radially outwards from the lead device. An inner diameter of the introducer is sufficiently greater than an outer diameter of the lead shaft (e.g., an embodiment of the lead shaft 110) with the surface elements 122 biased against their natural or relaxed state (e.g., surface areas of the surface elements 122 are approximately even with a remainder of a surface of the lead shaft) to allow the lead shaft to be moved through the introducer when the introducer is at or near a desired position within the body. At 1020, the introducer is extended into the body and located within the body at the desired position. At 1030, the lead device is pushed through the lumen of the introducer until the lead device is at the end of the introducer or extends beyond the introducer. At 1040, the introducer is removed, leaving the lead device at approximately the desired position within the body. At 1050, the lead device is moved (e.g., axially) and tested until it is determined that the lead device is properly positioned. Alternatively, at 1030 the lead device is pushed through the lumen of the introducer until it extends out of the introducer sufficiently to adjust the position of the lead device at the desired position, such as by imaging a marker on the distal end 117 of the lead device to aid in adjusting the position of the lead device (1050); then the introducer is removed (1040).

With reference to FIG. 9 and FIG. 10, when the introducer is removed, the surface elements 122 can release outward to their respective unbiased state. When present in the tissue, the introducer can form a void within the tissue, such that the removal of the introducer allows the surface elements 122 to extend outward. The surface elements 122 can be formed from material that is sufficiently resilient to allow the surface elements 122 to return to or near their respective unbiased state when deployed. By way of example, such materials may include silicone elastomer, polyurethane (e.g., 65D polyurethane, 75D polyurethane or other polymeric compound) or NITINOL (or other elastic memory alloy). In one or more embodiments, the surface elements 122 are caused to have the unbiased state by being subjected to pressure, force and/or heat during manufacture.

In one or more embodiments, one or more of the surface elements 122 are retained in a biased state by a degradable (e.g., dissolvable) material that is disposed under, over, and/or around the surface elements 122. When the lead device is positioned in the body at a target site (e.g., the introducer is removed), fluid at the target site begins to degrade (e.g., dissolve) the material; after a time, the surface elements 122 are unencumbered by the material and are allowed to return to or near their respective unbiased state. In this manner, some or all of the surface elements 122 do not engage with tissue at the target site immediately; for example, retaining the surface elements 122 may allow for a simpler process of positioning a lead device within an introducer, or may allow for fine-tuning of the position of a lead device at a target site prior to release of the surface elements 122.

Figure 11:
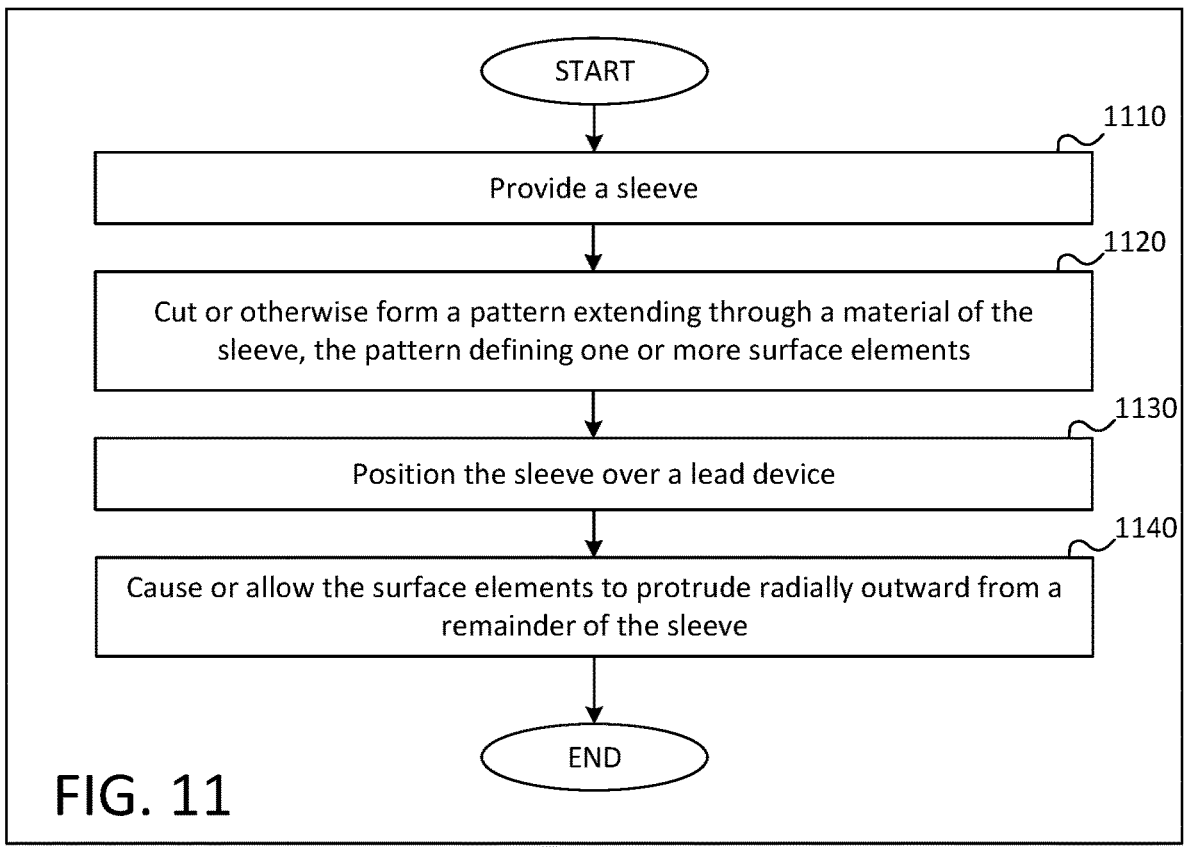
FIG. 11 illustrates a method for manufacturing surface elements on a sleeve for a lead device, according to one or more embodiments.

FIG. 11 illustrates a method for providing surface elements on a sleeve for a lead device, according to one or more embodiments. At 1110, a sleeve is provided. At 1120, a pattern is cut or otherwise formed in a material of the sleeve, where the pattern extends through the material to define a patterned sleeve (e.g., an embodiment of the patterned sleeve 120) with multiple surface elements (e.g., embodiments of surface elements 122). At 1130, the patterned sleeve is positioned over a lead device (e.g., an embodiment of the lead device 105). At 1140, the surface elements are caused or allowed to protrude radially outward from a remainder of the sleeve, such as described below.

Figure 12:
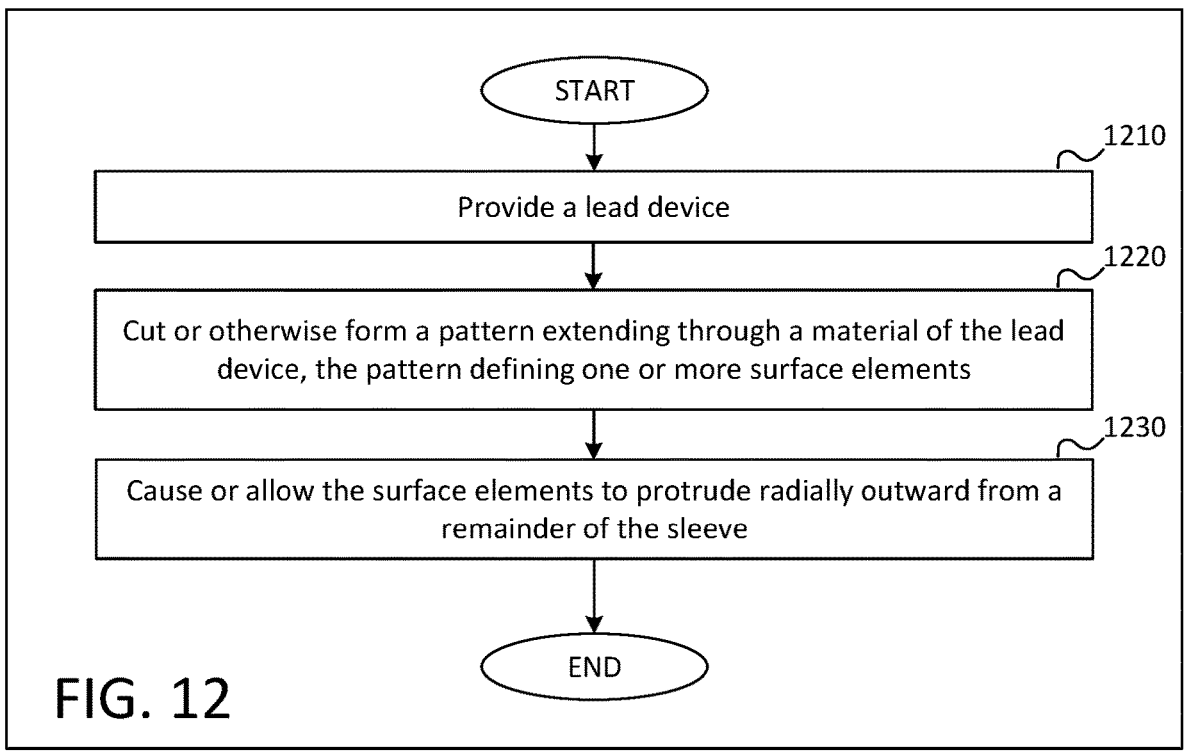
FIG. 12 illustrates a method for manufacturing surface elements on a lead device, according to one or more embodiments.

FIG. 12 illustrates a method for manufacturing surface elements on a lead device, according to one or more embodiments. At 1210, a lead device (e.g., an embodiment of the lead device 105) is provided. At 1220, a pattern is cut or otherwise formed in a material of the lead device, where the pattern extends through the material to define a pattern with multiple surface elements (e.g., embodiments of surface elements 122). At 1230, the surface elements are caused or allowed to protrude radially outward from a remainder of the lead device, such as described below.

In embodiments, the surface elements 122 may be formed through the creation of one or more slits that allow a thickness of the perimeter shell 118 to be manipulated so as to protrude outward.

According to one or more embodiments, at least a portion of the perimeter shell 118 may be formed from flexible or resilient material, such as silicone elastomer, polyurethane (e.g., 65D polyurethane, 75D polyurethane or other polymeric compound) or NITINOL (or other elastic memory alloy). The structure of the perimeter shell 118 may allow individual surface elements 122 to be unitarily formed as resilient and flexible extensions, while allowing for the surface elements 122 to be moveable inwards under bias and then releasable outwards.

According to one or more embodiments, biodegradable sleeves (e.g., embodiments of the patterned sleeve 120) may be constructed in one or more layers, and each layer may include one or more biodegradable materials. Examples of biodegradable materials that may used in embodiments of the present disclosure include without limitation polymers (such as but not limited to poly(lactic acid) (PLA), poly (glycolic acid) (PGA), poly(lactic-co-glycolic acid) (PLGA), polyethylene glycol (PEG), polycaprolactone (PCL), a combination of any of the foregoing polymers with another material or materials, and combinations of any two or more of the foregoing), metals (such as but not limited to magnesium (Mg), iron (Fe), tungsten (W), zinc (Zn), yttrium (Y), neodymium (Nd), zirconium (Zr), palladium (Pd), manganese (Mn), a combination of any of the foregoing metals with another material or materials, an alloy of any the foregoing metals, or a combination of two or more of any of the foregoing), metallic glasses (such as but not limited to those based on strontium (Sr) or calcium (Ca)), starch, other biodegradable materials, and any combination of two or more of the foregoing. The biodegradable materials may be selected based on desired properties for the particular medical apparatus (e.g., embodiments of the medical apparatus 100), such as rate of biodegradation, shear strength prior to or during biodegradation, brittleness, tensile strength, durability, bendability, manufacturability of the apparatus incorporating the biodegradable material(s), compatibility with other materials used in the apparatus, material stability (e.g., shelf life), temperature constraints, acidity constraints, and so forth.

According to one or more embodiments, sleeves (e.g., embodiments of the patterned sleeve 120) may be constructed in one or more layers. Each layer may include one or more materials. Each layer may include either biodegradable materials or non-biodegradable materials, or a combination of biodegradable materials and non-biodegradable materials. Thus, a sleeve as initially deployed at a target site may be structurally different than the same sleeve at a later time as biodegradable portions biodegrade, allowing for an adaptive design as tissue forms around surface elements (e.g., embodiments of the surface elements 122) on the sleeve.

According to one or more embodiments, whatever material is used to form surface elements (e.g., embodiments of the surface elements 122), exterior surfaces of the surface elements may be roughened mechanically, thermally or chemically to increase the resistance of the surface elements to movement.

According to one or more embodiments, exterior surfaces of the surface elements may be chemically coated to increase the resistance of the surface elements to movement and/or to promote tissue growth around the surface elements.

Although surface elements (e.g., embodiments of the surface elements 122) are illustrated herein as being positioned facing towards or away from a distal end of a lead device (e.g., the distal end 117 of the lead device 105) for ease of illustration, in one or more embodiments all or a portion of the surface elements may face in a different direction. For example, if facing towards the distal end is defined as a zero-degree rotation angle(0°) and facing opposite the distal end is defined as a one hundred eighty-degree rotation angle (180°), one or more surface elements may be at any rotation angle 0° to 180° or 180° to 360°. Moreover, a lead device may include surface elements at each of several different rotation angles, to resist movement in multiple directions.

FIG. 13 illustrates an example of a lead device with multiple surface elements arranged unidirectionally. A lead shaft 1310 includes a perimeter shell 1315 with surface elements 1320 cut into the perimeter shell 1315. The lead shaft 1310 further includes markers 1325 which may be used for identifying a position of the lead shaft 1310 during and after introduction into a body, such as through use of imaging techniques. In various versions of the lead shaft 1310, one or both of the markers 1325 are electrically connected to wires 1330 running through a length of the lead shaft 1310 to electrodes (not shown) configured to be inserted or otherwise mechanically and electrically connected to a controller (not shown) for providing electrical signals through the wires 1330 to the marker(s) 1325, such as for treatment or diagnosis. In the example illustrated in FIG. 13, the perimeter shell 1315 is an outer portion of the material forming the lead shaft 1310; in other examples, the perimeter shell is implemented as a sleeve positioned over the lead shaft 1310. The surface elements 1320 face a same direction (e.g., towards either a distal end or a proximal end of the lead shaft 1310.) In an embodiment, the perimeter shell 1315 was formed from a polyethylene or polyetheretherketone tube incorporating injected molded VESTA-KEEP® I-grade material available from Evonik. The markers 1325 were 90/10 platinum/iridium.

FIG. 14 illustrates an example of a lead device with multiple surface elements arranged bidirectionally. A lead shaft 1410 includes a perimeter shell 1415 with surface elements 1420 cut into the perimeter shell 1415. The lead shaft 1410 further includes markers 1425 which may be used for identifying a position of the lead shaft 1410 during and after introduction into a body, such as through use of imaging techniques. In various versions of the lead shaft 1410, one or both of the markers 1425 are electrically connected to wires 1430 running through a length of the lead shaft 1410 to electrodes (not shown) configured to be inserted or otherwise mechanically and electrically connected to a controller (not shown) for providing electrical signals through the wires 1430 to the marker(s) 1425, such as for treatment or diagnosis. In the example of FIG. 14, the perimeter shell 1415 is an outer portion of the material forming the lead shaft 1410; in other examples, the perimeter shell is implemented as a sleeve positioned over the lead shaft 1410. A first portion of the surface elements 1420 (identified as 1420a) face a first direction (e.g., towards a distal end of the lead shaft 1410), a second portion of the surface elements 1420 (identified as 1420b) face in a second direction opposite the first direction (e.g., towards a proximal end of the lead shaft 1410), and none of the visible surface elements 1420a and surface elements 1420b face each other. In other examples, surface elements are arranged such that at least two surface elements face each other. The perimeter shell 1415 was formed from a polyethylene or polyetheretherketone tube incorporating injected molded VESTAKEEP® I-grade material available from Evonik. The markers 1425 were 90/10 platinum/iridium.

Several prototypes were tested in fresh sheep cadaver tissue. Table 1 provides pull force test results for three categories of prototypes, with four prototypes each (n=4). The three categories were: (i) no surface elements, (ii) unidirectional surface elements similar to FIG. 13 (pulled in a direction approximately parallel to arrow Z1), and (iii) bidirectional surface elements similar to FIG. 14 (pulled in a direction approximately parallel to arrow Z2). The prototypes with no surface elements had low pull force (0.2 pound force (1 bf) average), which could result in a high risk of lead migration. The prototypes with unidirectional surface elements similar to those shown in FIG. 13 had a higher pull force (1.2 1 bf average) than the prototype with no surface elements, and the prototypes with bidirectional surface elements similar to those shown in FIG. 14 had a slightly higher pull force (1.5 1 bf average) than the unidirectional surface elements similar to those shown in FIG. 13.

TABLE 1

| Type | Average Peak Pull Force (lbf) |
| --- | --- |
| No surface elements | 0.2 |
| Unidirectional (similar to FIG. 13) | 1.2 |

TABLE 1-continued

| Type | Average Peak Pull Force (lbf) |
| --- | --- |
| Bidirectional (similar to FIG. 14) | 1.5 |

It is expected that surface elements such as shown in FIG. 13 and FIG. 14 have sufficiently high pull force to minimize or prevent migration, while also allowing for extraction of the lead without breakage when it is desired to remove the lead. The avoidance of breakage can, for example, avoid invasive surgical procedures to extract remnants of a broken lead.

It is further expected that bidirectional surface elements similar to those shown in FIG. 14 will minimize or prevent migration both distally and proximally, such as for target sites in which distal and proximal migration is expected or possible.

Figure 15A:
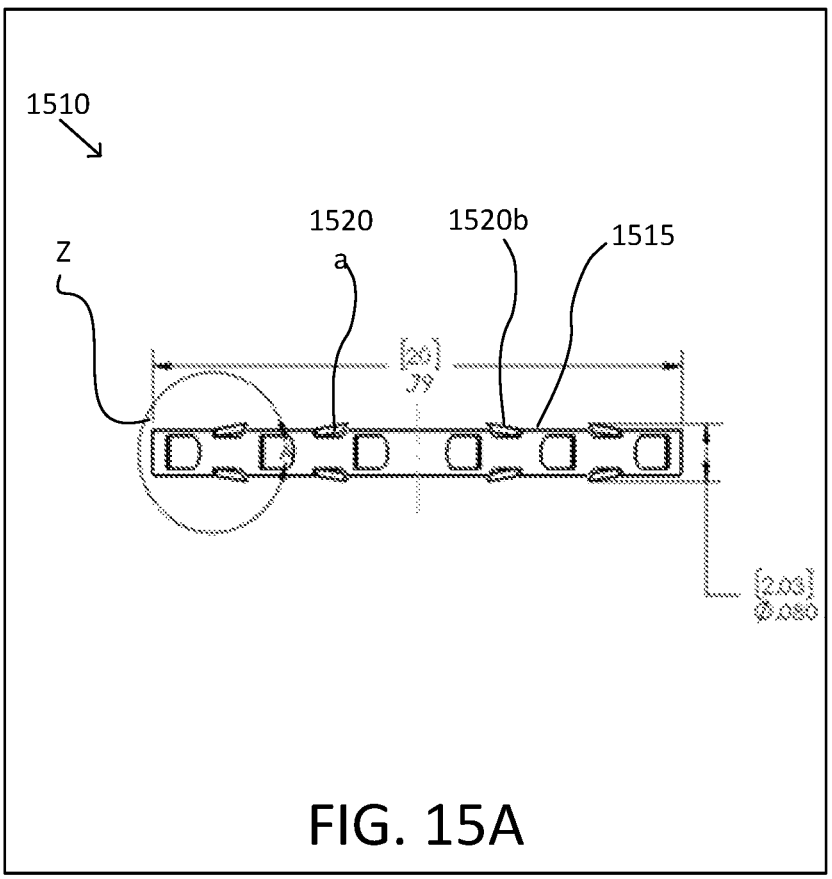
FIG. 15A through FIG. 15D illustrate an example of a lead device with multiple surface elements arranged bidirectionally.
Figure 15B:
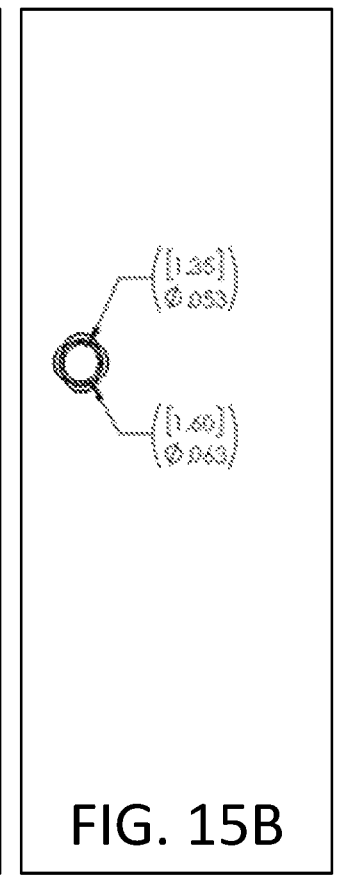
Figure 15C:
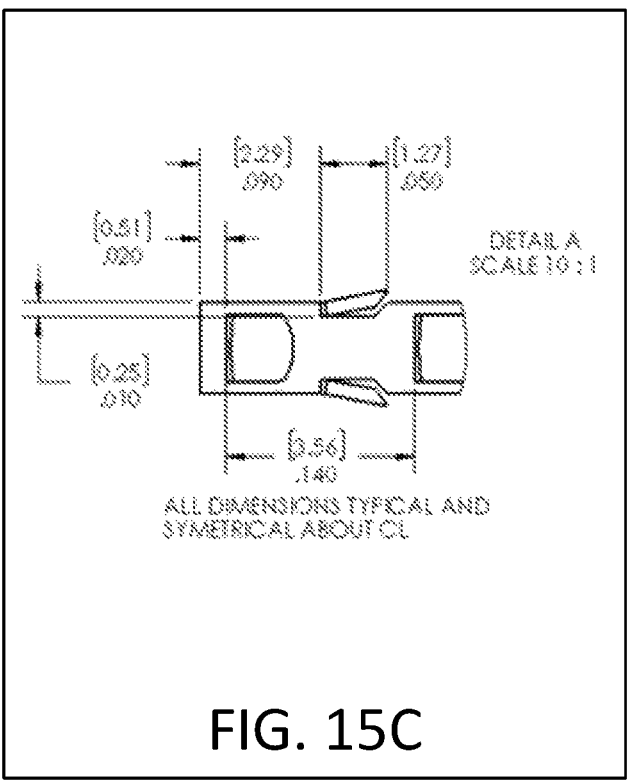
Figure 15D:
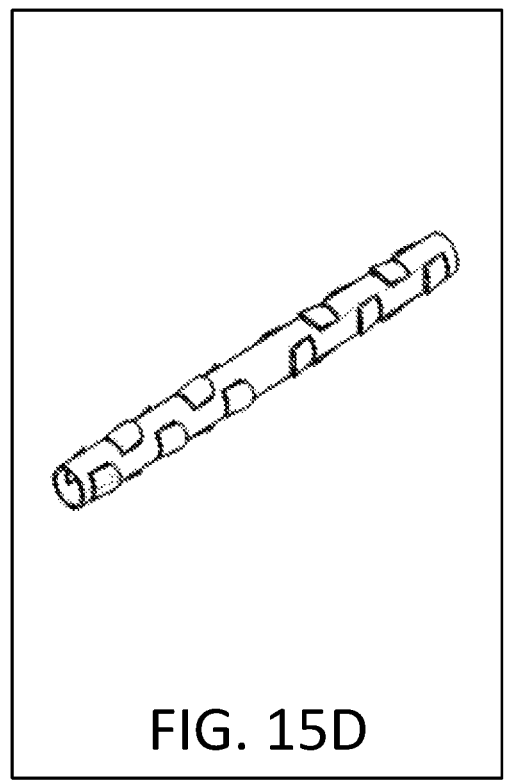

FIG. 15A through FIG. 15D illustrate an example of a patterned lead shaft 1510 with multiple surface elements arranged bidirectionally. FIG. 15A illustrates a side view of the lead shaft 1510; FIG. 15B illustrates an end view of the lead shaft 1510; FIG. 15C illustrates a closeup of Section Z of FIG. 15A; and FIG. 15D is an isometric view of the lead shaft 1510. The lead shaft 1510 includes a perimeter shell 1515 that includes surface elements 1520 cut into its perimeter thickness. The perimeter shell 1515 may be integral with the lead shaft 1510 or may be a sleeve.

A first portion of the surface elements 1520 (shown as 1520a) face a first direction (e.g., towards a proximal end of the lead shaft 1510), a second portion of the surface elements 1520 (shown as 1520b) face in a second direction opposite the first direction (e.g., towards a distal end of the lead shaft 1510), and the surface elements 1520a face the surface elements 1520b. Without being bound by theory, it is expected that the arrangement of the bidirectional surface elements 1520a/1520b facing each other in FIG. 15A through FIG. 15D will provide a resistance against movement similar to the bidirectional surface elements 1420a/1420b facing away from each other in FIG. 14, and that the bidirectional surface elements 1520a/1520b would be more easily positioned within an introducer than would the bidirectional surface elements 1420a/1420b.

The examples illustrated in FIG. 13, FIG. 14, and FIG. 15A through FIG. 15D are reminiscent of fish scales in a tactile sense, meaning that when the lead shafts 1310/1410/1510 are rubbed in a direction such that the surface elements 1320/1420/1520 are moved towards a bias direction (e.g., flat against the perimeter shell 1315/1415/1515), the lead shafts 1310/1410/1510 have a somewhat smooth feel; however, when the lead shafts 1310/1410/1510 are then rubbed in a direction such that the surface elements 1320/1420/1520 are moved against the bias direction (e.g., to protrude more from the perimeter shell 1315/1415/1515), the lead shafts 1310/1410/1510 have a noticeably rougher feel as tips of the surface elements make contact with skin.

The examples illustrated in FIG. 13, FIG. 14, and FIG. 15A through FIG. 15D include non-degradable materials. Other examples additionally include degradable materials.

The examples illustrated in FIG. 13 and FIG. 14 include markers 1325 and 1425, respectively, which may be used for positioning. In other embodiments, a radiopaque material can be coated onto at least one of the surface elements, or at least one of the surface elements include a radiopaque material, to form markers for positioning. In yet further embodiments, a radiopaque material can be coated onto the lead shaft next to or under at least one of the surface elements to form markers for positioning.

As illustrated and described with respect to FIG. 9, an introducer may be used to position a lead device within a body, holding surface elements in a biased position within the introducer until released.

Figure 16A:
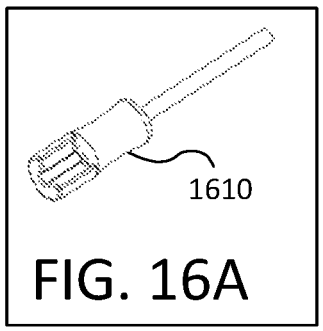
FIG. 16A, FIG. 16B, and FIG. 16C illustrate an example of a lead shaft being disposed in a loading tool.
Figure 16B:
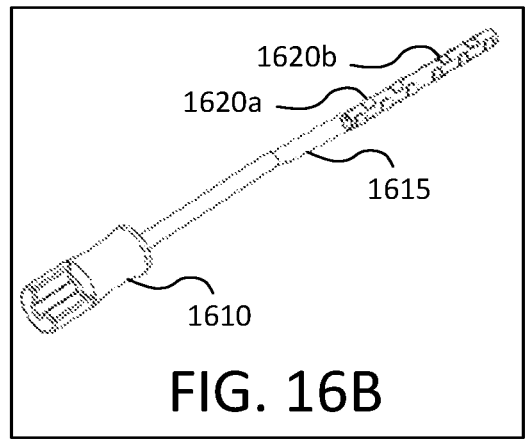
Figure 16C:
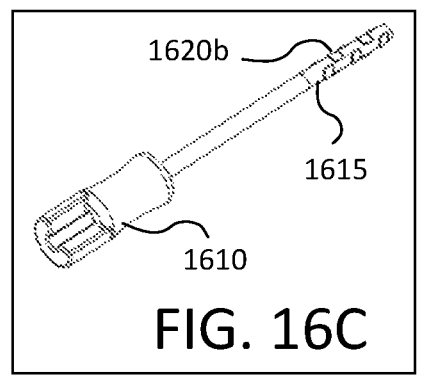

FIG. 16A, FIG. 16B, and FIG. 16C illustrate an example of a loading tool 1610 being positioned to bias certain ones of the surface elements inward for placement of the lead device into an introducer. In this example, the loading tool 1610 is provided (FIG. 16A), and a lead shaft 1615 is positioned within the loading tool (FIG. 16B, FIG. 16C) to bias certain ones of the surface elements 1620, which are illustrated as a set of surface elements 1620*a* and a set of surface elements 1620*b*. In the case of unidirectional surface elements (e.g., as in FIG. 13), the lead shaft 1615 may be disposed fully within the loading tool 1610. The lead shaft 1615 may be disposed partially within the loading tool 1610, to bias the surface elements 1620*a* and not the surface elements 1620*b* (FIG. 16C), such as in the case of bidirectional surface elements (e.g., as in FIG. 15) where the surface elements 1620*a* face the surface elements 1620*b*. The loading tool 1610 is then used to position the lead shaft 1615 into an introducer.

Figure 17A:
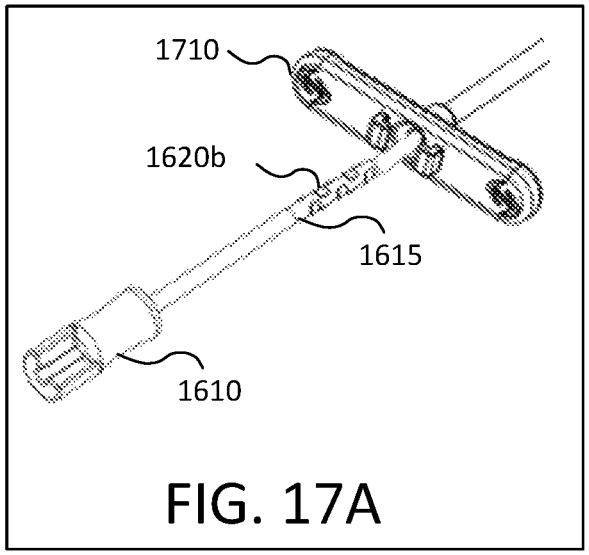
FIG. 17A and FIG. 17B illustrate an example of a loading tool for advancing a lead shaft into an introducer.
Figure 17B:
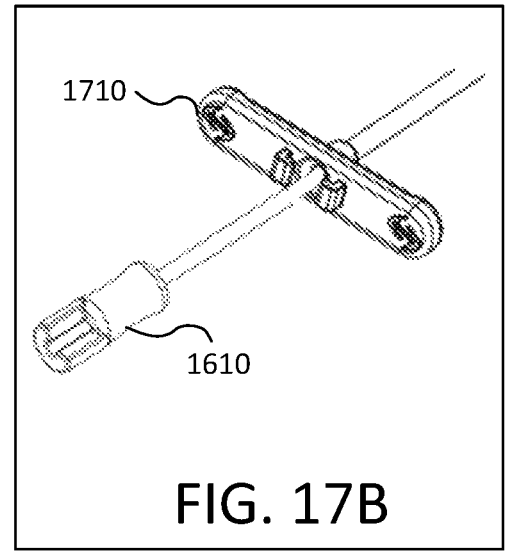
Figure 18:
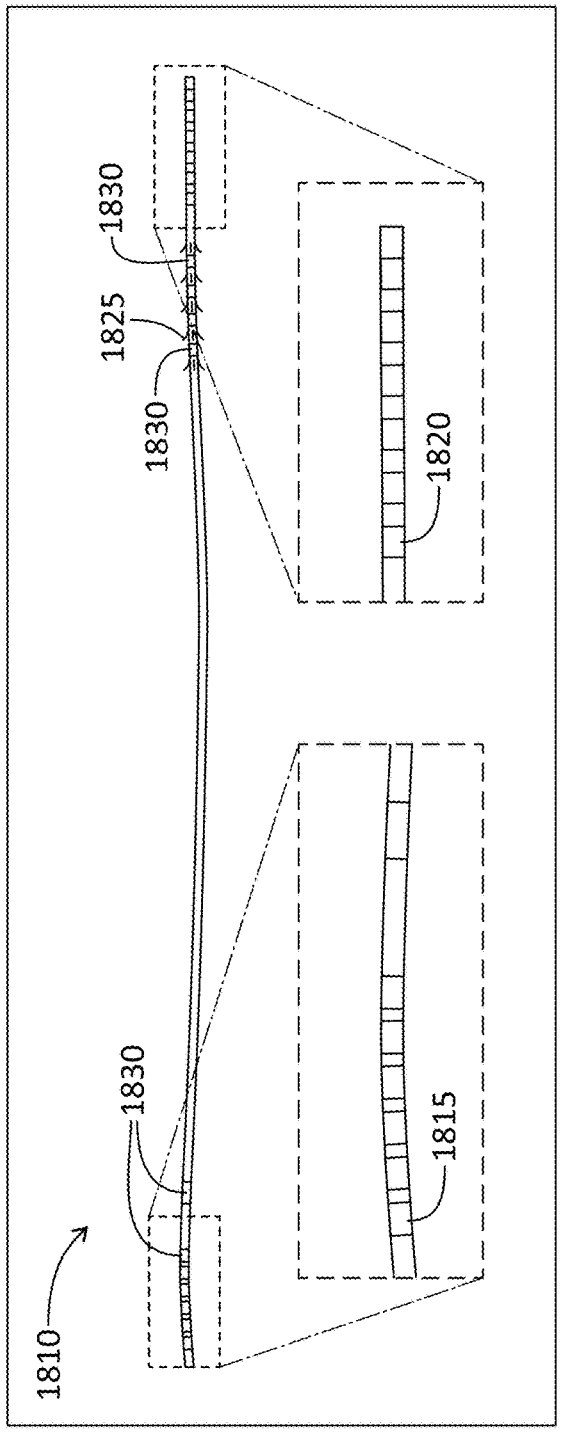

FIG. 17A and FIG. 17B illustrate an example of the loading tool 1610 being used to position the lead shaft 1615 within a lumen of an introducer 1710. In this example, surface elements 1620*b* face towards a handle of the loading tool 1610 and thus away from the introducer 1710. Accordingly, as the lead shaft 1615 is advanced into the introducer 1710 by the loading tool 1610 (FIG. 17A), the surface elements 1620*b* are biased against the body of the lead shaft 1615 by the lumen of the introducer 1710. As the lead shaft 1615 is advanced further into the introducer 1710 by the loading tool 1610, the loading tool 1610 also enters the lumen of the introducer 1710 (FIG. 17B). When the portion of the loading tool 1610 that covers the surface elements 1620*a* is disposed within the introducer 1710, the loading tool 1610 can be withdrawn, allowing the surface elements 1620*a* to be retained in a biased position by the introducer 1710. The introducer 1710 can then be positioned at a target delivery site, and the introducer 1710 removed to place the lead associated with the lead shaft 1615 at the target site. The surface elements 1620 (e.g., 1620*a*, 1620*b*) are then allowed to extend to an unbiased state.

FIG. 1B illustrates an example lead device 1810 that is approximately 29.3 centimeters (cm) in length and approximately 1.3 mm in diameter. The lead device includes six platinum/iridium contacts 1815 at a proximal end for mating with a connector of a stimulation controller. Each contact 1815 is approximately 1.6 mm in length, and the contacts are spaced approximately 0.9 mm apart. The lead device also includes six platinum/iridium contacts 1820 at a distal end for stimulating at a target site. Each contact 1820 is approximately 2 mm in length, and the contacts are spaced approximately 3 mm apart. The lead device 1810 further includes a set of unidirectional surface elements 1825 for resisting movement, and markers 1830 for positioning the lead device 1810 during initial placement or subsequent repositioning.

Figure 19:
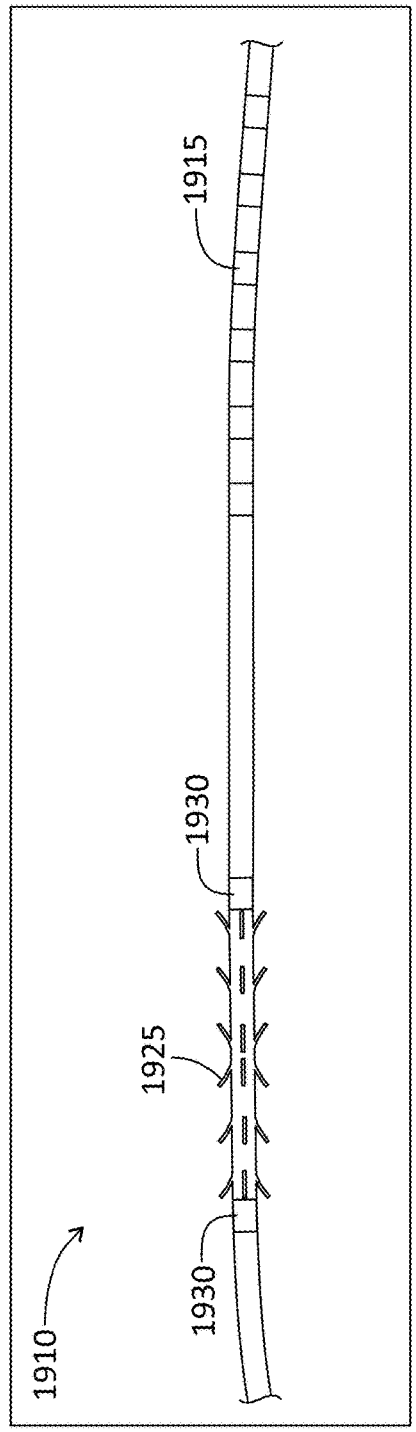
FIG. 19 illustrates an example of a lead device.

FIG. 19 illustrates a distal end of an example lead device 1910 including contacts 1915, a set of bidirectional surface elements 1925, and markers 1930.

In any embodiment of the present disclosure, an optional coating may be applied over surface elements, and/or an optional adhesive material may be applied between the surface elements and the lead shaft, to temporarily maintain a bias of the surface elements to facilitate placement within an introducer. Upon removal of the introducer from the body, the optional coating and/or optional adhesive material is exposed to body matter and dissolves. The dissolution rate can be designed to release the surface elements from bias after a time, such as minutes, hours, or days after the introducer is removed. The optional coating and/or optional adhesive material can be, for example, any one or combination of the biodegradable materials discussed above.

In any embodiment of the present disclosure, geometry, length and bend angle of the surface elements may be adjusted to achieve the tissue engagement and holding power (resistance against movement) desired for the planned therapy.

In any embodiment of the present disclosure, resorbable materials such as PLA, poly(glycolic acid) (PGA), PLC, other material, or a combination of the foregoing, can be formed as a tube with the fixation geometry (surface elements) added to or formed in or on the tube. Materials could also include metals.

Surface elements may be described in the present disclosure as being positioned along surfaces of lead devices to minimize or prevent movement (e.g., migration) of the lead devices, such as leads for urinary tract stimulus (e.g., stimulus along a pudendal or sacral nerve or trunk, stimulus to the external urinary sphincter or anal sphincter, or stimulus to detrusor muscles), cardiac stimulus, stimulus for pain control, and stimulus to various other tissue (e.g., other nerve, muscle, or bone tissue). However, surface elements such as described in the present disclosure are also suitable for preventing movement of many other types of implantable devices.

Embodiments of the present disclosure include without limitation the following aspects:

In an aspect, a lead device of a medical device includes a first set of surface elements and a second set of surface elements. The first set includes one or more biodegradable surface elements configured to protrude from the lead device upon deployment, and the first set is designed to resist movement of the lead device upon deployment and for a designed time thereafter until the first set biodegrades in vivo. The second set includes one or more non-biodegradable surface elements configured to protrude from the lead device upon deployment; the second set is designed to promote tissue growth around the surface elements within the designed time for the first set to biodegrade in vivo.

In an aspect, a lead device of a medical device includes a lead shaft, an electrode, a patterned sleeve, and biodegradable surface elements on the patterned sleeve. The lead shaft includes a perimeter shell having a fixation region and a treatment region, and the lead shaft defines a channel configured to accept at least one electrical conductor. The electrode is positioned in the treatment region, and is configured to be electrically connected to the conductor. The patterned sleeve forms a portion of the fixation region of the perimeter shell. Each biodegradable surface element is designed to resist movement of the lead device upon deployment and for a designed time thereafter until biodegradation of the biodegradable surface element.

In an aspect, a lead device of a medical device includes a lead shaft including a perimeter shell having a fixation region and a treatment region, an electrode in the treatment region, non-biodegradable surface elements disposed in the fixation region, and a biodegradable sleeve covering the non-biodegradable surface elements. The biodegradable sleeve may be configured to biodegrade over a predefined time period such that at the end of the time period the biodegradation has progressed sufficiently to allow the non-biodegradable surface elements to be released from a biased state. The non-biodegradable surface elements may be held in the biased state by the presence of the biodegradable sleeve, and after being released from the biased state protrude from the perimeter shell.

In an aspect, a sleeve for a lead device of a medical device includes a perimeter shell including a first end and a second end, the perimeter shell defining an interior space to receive a lead shaft, and surface elements that project outward from an exterior surface of the perimeter shell, each surface element including a base that is integrated with or connected to the exterior of the perimeter shell, and an end segment which is separated from the perimeter shell by a separation distance that is of an order of magnitude of a thickness of the surface element.

In an aspect, a lead device of a medical device includes a perimeter shell including a first end and a second end, the perimeter shell defining an interior space to receive a lead shaft, and surface elements that project outward from an exterior surface of the perimeter shell, wherein the surface elements are formed by a corresponding combination of slits in the perimeter shell that allow the surface element to project outward.

In an aspect, a lead device of a medical device includes a lead shaft, a perimeter layer including a first end and a second end, the perimeter layer defining an interior space to receive a lead shaft, and surface elements that project outward from an exterior surface of the perimeter layer, wherein the plurality of surface elements is formed by a corresponding combination of slits in the perimeter layer that allow the surface element to project outward.

In an aspect, a method for operating a medical device includes: covering a portion of a lead body with a sleeve, the sleeve including a perimeter shell and surface elements that project outward from an exterior surface of the perimeter shell, wherein the surface elements are formed by a corresponding combination of slits in the perimeter shell that allow the surface element to project outward; encapsulating the sleeve and the lead body with an introduction device; advancing the introduction device with the encapsulated sleeve and lead body through a patient's tissue, until the lead body reaches a target region within the patient's tissue; and when the lead device reaches the target region, removing the introduction device to cause the plurality of surface elements to release and extend outward beyond a dimension that was previously occupied by the introduction device.

An embodiment of any of the foregoing aspects may include without limitation one of, or a combination of, the following features:

Surface elements each include a strip of material attached at one end or both ends of the strip to the lead device, thereby forming a void between the strip and the lead device. The strip of material and the void are designed to promote tissue growth around the surface element, including within the void. A joint connects the strip and the lead device. The joint may be designed to break after tissue growth has occurred around the surface element, and upon exertion of a pulling force axially along the lead device.

A surface element includes a metal. The metal may be magnesium.

A surface element includes a polymer. The polymer may be one or both of poly(lactic acid) (PLA) or polycaprolactone (PCL).

A perimeter shell of a lead device includes non-biodegradable surface elements. Each non-biodegradable surface element is shaped to promote tissue growth around and through the non-biodegradable surface element.

A lead device includes multiple treatment regions of the perimeter shell.

A lead device includes multiple fixation regions of the perimeter shell.

A lead device includes at least one fixation region interspersed between multiple treatment regions.

Biodegradable surface elements are disposed on a biodegradable sleeve, and the biodegradable surface elements are configured to engage tissue at a target site when deployed such that the lead device resists movement.

A thickness of a surface element is less than or equal to a thickness of a perimeter shell of the lead device.

The surface elements are formed by a corresponding combination of slits in the perimeter shell that allow the surface element to project outward.

Each of the surface elements has a polygonal shape, with at least a portion of the polygonal shape being separated from the surface of the perimeter shell by a corresponding combination of slits. The polygonal shape may be rectangular, and the combination of slits may define at least three sides of the polygonal shape.

A surface element projects outward from a perimeter shell by an angle that is less than 10 degrees.

A surface element projects over a recess formed in the perimeter shell.

The surface elements include a first set of surface elements that have a first orientation that is of a first longitudinal direction, and a second set of surface elements that have a second orientation that is of a second longitudinal direction. In the first orientation, a projected tip portion of the surface element is forward-facing, coinciding with a direction in which the lead device is introduced into the patient's tissue, and in the second orientation, the projected tip portion of the surface element is rear-facing, coinciding with a reverse of the direction in which the lead device is introduced into the patient's tissue.

A shell structure includes (i) a first radial element that includes multiple surface elements of only a first set of elements, and (ii) a second radial element that includes multiple surface elements of only a second set of elements. The first radial element of the shell structure may be offset from the second radial element of the shell structure by about 90 degrees. Each surface element that is included with the first radial element may be longitudinally offset from at least one surface element that is included with the second element. The shell structure may further include (i) a third radial element that is offset from the first radial element by about 180 degrees, the third radial element including multiple surface elements of only the first set of elements, and (ii) a fourth radial element that is offset from the second radial element by about 180 degrees, the fourth radial element including multiple surface elements of only the second set of elements. Some of the multiple surface elements that are included with the first radial element may be longitudinally aligned with a corresponding surface element that is included with the third radial element A perimeter shell is unitarily formed as part of a lead device.

Selecting at least one of a length, width or thickness of a surface element based on a predetermined condition. The predetermined condition may be a longitudinal direction of the surface element when in a deployed position. The predetermined condition may be a characteristic of the patient's tissue. The predetermined condition may be an expected duration in which the lead device is to remain within the tissue of a patient.

A target stiffness is designed for a surface element, and at least one of a length, width or thickness of the surface element is based on the identified target stiffness.

It is contemplated for examples described herein to extend to individual elements and concepts described herein, independently of other concepts, ideas or system, as well as for examples to include combinations of elements recited anywhere in this application. Although examples are described in detail herein with reference to the accompanying drawings, it is to be understood that the concepts are not limited to those precise examples. Accordingly, it is intended that the scope of the concepts be defined by the following claims and their equivalents. Furthermore, it is contemplated that a particular feature described either individually or as part of an example can be combined with other individually described features, or parts of other examples, even if the other features and examples make no mention of the particular feature. Thus, the absence of describing combinations should not preclude having rights to such combinations. Moreover, although described with respect to a lead device, the anchoring mechanisms of the present disclosure may be used for anchoring other medical implants, and although described with respect to medical implants, the anchoring mechanisms of the present disclosure may be used in other areas or fields.

What is claimed is:

1. A lead device of a medical device, the lead device comprising:
   a lead shaft comprising a perimeter shell having a fixation region and a treatment region, wherein at least a portion of the perimeter shell is biodegradable; and
   an electrode in the treatment region;
   wherein the perimeter shell includes a plurality of surface elements disposed in the fixation region, the plurality of surface elements including
      a first set of surface elements comprising one or more biodegradable surface elements configured to protrude from the lead device upon deployment, the first set of surface elements being structured to resist movement of the lead device upon deployment and for a designed time thereafter until the first set of surface elements biodegrades in vivo; and
      a second set of surface elements comprising one or more non-biodegradable surface elements configured to protrude from the lead device upon deployment, the second set of surface elements being structured to promote tissue growth around the second set of surface elements within the designed time for the first set of surface elements to biodegrade in vivo.

2. The lead device of claim 1, wherein at least some of the plurality of surface elements disposed in the fixation region are non-biodegradable.

3. The lead device of claim 1, wherein the perimeter shell includes a biodegradable sleeve covering one or more non-biodegradable surface elements disposed in the fixation region.

4. The lead device of claim 3, wherein the sleeve is patterned to include a plurality of biodegradable surface elements in the fixation region, each biodegradable surface element being structured to resist movement of the lead device upon deployment and for a designed time thereafter until biodegradation of the biodegradable surface element.

5. The lead device of claim 3, wherein at least one of the non-biodegradable surface elements comprises a strip of non-biodegradable material, each end of the strip being attached to the perimeter shell at a respective joint, and at least one joint being configured to break when the lead device is subjected to a pulling force after tissue growth has occurred around and through the non-biodegradable surface element.

6. The lead device of claim 3, wherein the biodegradable sleeve is configured to biodegrade over a predefined time period such that at the end of the time period the biodegradation has progressed sufficiently to allow the one or more non-biodegradable surface elements to be released from a biased state.

7. The lead device of claim 6, wherein the one or more non-biodegradable surface elements are held in the biased state by the presence of the biodegradable sleeve, and after being released from the biased state protrude from the perimeter shell.

8. The lead device of claim 3, further comprising biodegradable surface elements disposed on the biodegradable sleeve, the biodegradable surface elements configured to engage tissue at a target site when deployed such that the lead device resists movement.

9. The lead device of claim 1, wherein the surface elements of the second set each comprise a strip of material attached at both ends of the strip to the lead device, thereby forming a void between the strip and the lead device, the strip of material and the void designed to promote tissue growth around the surface element, including within the void.

10. The lead device of claim 9, further comprising two joints for each surface element of the second set, one joint at each end of the strip where the strip is attached to the lead device, wherein at least one of the two joints associated with each surface element of the second set are designed to break, after tissue growth has occurred around the surface element, and upon exertion of a pulling force axially along the lead device.

11. The lead device of claim 1, wherein at least some of the surface elements of the first set comprise a metal.

12. The lead device of claim 11, wherein the metal comprises magnesium.

13. The lead device of claim 1, wherein at least some of the surface elements of the first set comprise a polymer.

14. The lead device of claim 13, wherein the polymer comprises one or both of poly (lactic acid) (PLA) or polycaprolactone (PCL).

15. The lead device of claim 1, further comprising multiple treatment regions of the perimeter shell, wherein the treatment region is a first treatment region of the multiple treatment regions.

16. The lead device of claim 1, further comprising multiple fixation regions of the perimeter shell, wherein the fixation region is a first fixation region of the multiple fixation regions.

17. The lead device of claim 16, further comprising a second fixation region of the multiple fixation regions, wherein the second fixation region comprises a plurality of non-biodegradable surface elements.

18. The lead device of claim 17, further comprising a plurality of non-biodegradable surface elements disposed in the first fixation region.

19. The lead device of claim 1, further comprising multiple treatment regions of the perimeter shell and multiple fixation regions of the perimeter shell, wherein the treatment region is a first treatment region of the multiple treatment regions and wherein the fixation region is a first fixation region of the multiple fixation regions.

20. The lead device of claim 19, wherein the multiple treatment regions are interspersed between ones of the multiple fixation regions.

* * * * *